United States Patent [19]

Opie et al.

[11] Patent Number: 4,997,084
[45] Date of Patent: Mar. 5, 1991

[54] PACKAGING SYSTEM FOR DISPOSABLE ENDOSCOPE SHEATHS

[75] Inventors: Eric Opie, Brier; Fred E. Silverstein, Seattle, both of Wash.

[73] Assignee: Opielab, Inc., Seattle, Wash.

[21] Appl. No.: 194,034

[22] Filed: May 13, 1988

[51] Int. Cl.⁵ .............................................. B65D 83/10
[52] U.S. Cl. .................................. 206/364; 206/438; 383/36
[58] Field of Search ...................... 206/364, 438, 484; 383/36, 37, 40, 33; 604/54, 263, 280; 128/4

[56] References Cited

U.S. PATENT DOCUMENTS

| | | | |
|---|---|---|---|
| 3,750,875 | 8/1973 | Juster | 206/364 |
| 3,797,734 | 3/1974 | Fleury et al. | 383/40 |
| 3,831,587 | 8/1974 | Boyd . | |
| 3,956,011 | 5/1976 | Carleton . | |
| 4,065,816 | 1/1978 | Sawyer | 206/438 |
| 4,182,478 | 1/1980 | Etes | 383/36 |
| 4,230,115 | 10/1980 | Walz, Jr. et al. | 206/438 |
| 4,256,102 | 3/1981 | Monaco | 604/280 |
| 4,299,244 | 11/1981 | Hirai . | |
| 4,550,440 | 10/1985 | Rico | 383/33 |
| 4,620,527 | 11/1986 | Adams, Jr. | 128/4 |
| 4,646,722 | 3/1987 | Silverstein et al. | 128/4 |
| 4,721,097 | 1/1988 | D'Amelio . | |
| 4,754,877 | 7/1988 | Johansson et al. | 206/364 |
| 4,772,275 | 9/1988 | Elich | 206/438 |
| 4,787,753 | 11/1988 | Barnhart | 383/33 |

FOREIGN PATENT DOCUMENTS

WO89/00832 7/1988 PCT Int'l Appl. .

Primary Examiner—David T. Fidei
Attorney, Agent, or Firm—Seed and Berry

[57] ABSTRACT

A system for packaging disposable endoscope sheaths so that they do not become contaminated prior to use during shipment, storage and installation on an endoscope. The packaging system also prevents the spread of contamination after use while the sheath is being removed from the endoscope and then discarded. The sheath is shipped in an elongated, flexible bag having a length substantially equal to the length of the insertion tube of the endoscope and a diameter substantially larger than the diameter of the insertion tube. The sheath and bag may be shipped in a sterile tray having a spiral recess containing the sheath, bag and funnel-like container or bag holding the tubing of the air, water, and suction channels. Installation of the sheath on the endoscope is accomplished by inflating the sheath while it is in the bag so that the sheath expands until it contacts the wall of the bag. The insertion tube is then inserted into the sheath, the sheath is deflated and the insertion tube and surrounding sheath are removed from the bag for use. After use, the insertion tube and surrounding sheath are inserted into the bag, and the sheath is inflated until it is restrained from further expansion by the wall of the bag. The insertion tube is then removed from the sheath, the sheath is deflated, and the sheath and surrounding bag are discarded as a unit, the funnel-like proximal segment being used to dispose of the contaminated tubes (air, water, suction, etc.).

10 Claims, 4 Drawing Sheets

PACKAGING SYSTEM FOR DISPOSABLE ENDOSCOPE SHEATHS

FIELD OF THE INVENTION

This invention relates to the field of endoscopy, and more particularly, to a system for packaging disposable endoscope sheaths before and after use so that the sheaths remain sterile until they are used and do not spread contamination after use.

BACKGROUND ART

The use of endoscopes for diagnostic and therapeutic indications is rapidly expanding. To improve performance, endoscopes have been optimized to best accomplish their purpose. Therefore, there are upper endoscopes for examination of the esophagus, stomach and duodenum; colonoscopes for examining the colon; angioscopes for examining blood vessels; bronchoscopes for examining the bronchi; laparoscopes for examining the peritoneal cavity; and arthroscopes for examining joint spaces. The discussion which follows will apply to all of these types of endoscopes.

Instruments to examine the rectum and sigmoid colon, known as flexible sigmoidoscopes, are good examples of the usefulness of endoscopic technology. These devices are expensive, and they are used in a contaminated environment for a procedure which is brief (5-10 minutes) and where problems of cleaning time and contamination are important factors. There has been a large increase in the use of the "flexible sigmoidoscope" for use in screening symptomatic and asymptomatic patients for colon and rectal cancer. Ideally, flexible sigmoidoscopes must be used rapidly and inexpensively in order to maintain the cost of such screening at acceptable levels. Typically, a clinic would like to perform five sigmoidoscope examinations each hour. A significant problem with making such examinations quick and inexpensive is the time necessary for adequately cleaning the device.

Although endoscopes can be superficially cleaned in about two to four minutes, this relatively cursory cleaning may not be adequate for complete disinfection and it does not sterilize 1 he instrument. Even a more complete cleaning requiring on the order of eight to ten minutes may not allow adequate cleaning, particularly in view of the increasing problems with contagious viruses. Even with the use of chemicals such as gluteraldehyde, depending on cleaning methods, adequate cleanliness may not be possible.

The cleaning problem not only includes the outside of the endoscope, but also the multiple small channels inside the endoscope. This includes channels for: air insufflation; water to wash the tip; and biopsy and suction. Each channel also has a control valve. The channels extend along the length of the endoscope and come into contact with body tissues and fluids. It is extremely difficult to adequately clean these channels even when skilled health practitioners spend a great deal of time on the cleaning procedure.

Even if endoscopes can be adequately cleaned in eight to ten minutes, the cleaning still prevents endoscopy examinations from being relatively inexpensive. While a physician may spend five to ten minutes performing some types of endoscopy, he or she will generally waste a great deal of time waiting for the endoscope to be cleaned before he or she can conduct another endoscopy. A partial solution to the "idle time" problem is to purchase multiple instruments so one can be used as the others are being cleaned. However, the expense of having duplicate, endoscopes of each of the many types described above makes this solution impractical especially for physicians' offices and smaller clinics.

Not only must the idle time of the physician be added to the cost of endoscopic examinations, but the time spent by a nurse or other hospital personnel in the cleaning as well as the cost of disinfecting chemicals and other costs of the cleaning process must also be added to the cost of the examination. Although automatic washing machines are available to clean endoscopes, these machines are expensive, take up significant amounts of space, are noisy and are not faster than washing by hand. Further, regardless of whether the cleaning is done manually or by machine, the cleaning chemicals can be harmful to the endoscope and thus significantly shorten its life span. The cleaning chemicals, being toxic, are also potentially injurious to the staff who use them, and to the environment into which they are discharged. To use some of these chemicals safely, such as gluteraldehyde, requires a dedicated ventilated hood, which uses up space and is expensive to install and operate. The chemicals are also potentially toxic to the patient in that, if residue remains after cleaning and rinsing the instrument, the patient could have a reaction to the chemicals.

As a result of these many problems, conventional endoscope cleaning techniques increase the cost of endoscopic procedures. Furthermore, while the risk of contamination using endoscopes is often far less than the risk of alternative procedures, such as surgery, there is nevertheless a risk that endoscopes are not adequately cleaned to prevent the risk of transmission of infectious diseases from one patient to the next.

In the health care field, the problems of contaminated instruments transmitting disease from one patient to the next have generally been solved by making such instruments disposable. However, this approach has not been thought possible in the field of endoscopy because endoscopes are expensive instruments. Moreover, it has not been thought possible to isolate the endoscope from the patient or the external environment because the endoscope itself has channels inside it that are used as a conduit for body fluids and tissues, such as, for example, in taking biopsies. The only method currently available to actually sterilize an endoscope is to use gas sterilization with ethylene oxide gas. However, there are several disadvantages in using this procedure. The procedure is very slow (up to 24 hours) during which the endoscope cannot be used. Also, the gas affects the plastic of the endoscope and shortens its life span. Finally, the gas is toxic, and, therefore, great care must be taken to ensure that no residue remains that might cause patient or staff, irritation or allergic reaction during contact with the endoscope.

The above-described limitations in cleaning endoscopes by conventional techniques limit the use of an endoscope. It is desirable to make endoscopy procedures both inexpensive and more free from risk of contamination.

A new approach to the problem of endoscope contamination is described in U.S. Pat. No. 4,646,722. This new approach involves the use of an endoscope sheath having a flexible tube surrounding the elongated core of an endoscope. The flexible tube has a transparent window near its distal end positioned in front of the viewing window of the endoscope. Channels that come into contact with the patient or the patient's body fluids, e.g. channels for taking biopsies, injecting air or injecting water to wash the window of the sheath, extend along the endoscope, either inside or outside the sheath. Where the channels are positioned inside the sheath, they may be inserted in a longitudinal groove formed in the endoscope core. The protective sheath may be used with either end-viewing endoscopes or side-viewing endoscopes. The protective sheath may be installed by rolling the elastomeric tube into an annular configuration and then unrolling the tube over the core of the endoscope. Alternatively, the tube may be inflated in its unrolled configuration to expand the tube and allow it to be easily slipped onto the endoscope core. A variety of specialized endoscopes may be created by using protective sheaths having a variety of special purpose medical instruments mounted at the end of a biopsy channel and operated through the channel.

One aspect of using protective endoscope sheaths that must be adequately dealt with is their handling both before and after use. The sheaths must be protected from becoming contaminated prior to use so that they do not contaminate or infect patients during endoscopy, particularly those having a depressed immune system. Consequently, the sheath should be packaged in a clean or sterile container during shipment and storage. It is also important that the sheath not become contaminated while it is being unpackaged and installed on an endoscope.

After the endoscopic examination has been completed, the outside of the sheath and its internal channels (i.e. biopsy channel, air and water channels), etc.) are contaminated with stool, blood or mucus. This contamination must not be spread around the examining room environment as the sheath is being removed from the endoscope and before it is placed in a suitable disposal receptacle.

DISCLOSURE OF THE INVENTION

It is an object of the invention to provide a system for packaging disposable endoscope sheaths that prevents them from becoming contaminated during shipment and installation on endoscopes.

It is another object of the invention to provide a system for packaging disposable endoscope sheaths that can be used to quickly and easily install the sheaths on endoscopes without contaminating the sheaths.

It is another object of the invention to provide a packaging system for disposable endoscope sheaths that prevents the sheaths from spreading contamination after use.

It is still another object of the invention to provide a packaging system for disposable endoscope sheaths that allows endoscopes to be easily and quickly removed from the sheaths after use.

It is a further object of the invention to provide a packaging system for disposable endoscope sheaths that can be adapted for use with a wide variety of endoscope sizes.

These and other objects of the invention are provided by a packaging system for a disposable endoscope sheath using an elongated or tubular bag with a closed end, made of flexible, nonelastic material. The tubular bag has a length that is slightly longer than the length of an endoscope insertion tube on which the sheath is to be installed and a diameter that is larger than the diameter of the insertion tube. The disposable sheath is positioned within the tubular bag with its open end positioned near the proximal end of the tubular bag so that the sheath can be installed on the insertion tube by inserting the insertion tube through the proximal opening in the tubular bag and the opening in the sheath.

The tubular bag may include a funnel or bag member that has an opening extending from the perimeter of the tubular bag adjacent to its proximal end. A funnel or large opening bag makes it easier to insert the endoscope into the tubular bag for placing the sheath onto the endoscope and removing the sheath when the sheath is to be disposed of. The bag also packages the tubing connections that connect the air, water, and suction tubes from the sheath to the endoscope. The bag may be retracted after the tubing has been removed and the endoscope inserted into the sheath without using a funnel member.

A rigid cylindrical collar preferably extends around the periphery of the tubular bag adjacent to the proximal end of the tubular bag. The rigid collar makes it easier to connect the bag elements to support the assembly in the vertical position.

In order to assist in the installation and removal of the sheath, a stand may be used to support the tubular bag in an extended, upright condition. The stand includes a vertically extending support bar and a support arm projecting horizontally from the vertical support bar. A forked member, or alternatively a collet, is coupled to the support arm to accept the tubular bag. The stand may also include a two-member arm above the tubular bag support arm to support an opening bag or funnel in an upright and open position. The two-member arm may be moved down the bar to pull the bag top downward to permit easier insertion of the endoscope into the tubular bag.

The tubular bag and sheath may be packaged in a tray having a base in which a spiral recess is formed. The recess has a length and width that are larger than the length and diameter of the bag so that the bag and sheath may be inserted into the recess to form a spiral or circular coil.

The sheath is installed by first inserting the tip of the endoscope into the open end of the sheath and then inflating the sheath until it expands to contact the inner wall of the bag. The bag thus restricts the expansion of the sheath to a diameter that is substantially equal to the diameter of the bag. The insertion tube of the endoscope is then inserted into the open end of the sheath while the sheath is in its expanded condition in the bag. Once the endoscope has been fully inserted, the sheath is allowed to deflate which causes the sheath to contract away from the wall of the bag and onto the outer surface of the insertion tube. Finally, the insertion tube and surrounding sheath are removed from the tubular bag so that the endoscope can be used to conduct an endoscopic examination or procedure. After the procedure, the sheath is removed from the endoscope. This is done by inserting the endoscope insertion tube, and surrounding sheath, into the proximal end of the tubular bag. The sheath is then inflated until is expands away from the surface of the insertion tube to contact the inner wall of the tubular bag. The insertion tube is then removed from the open end of the sheath while the sheath is in its expanded condition in the tubular bag. The sheath is then deflated to allow the sheath to contract away from the wall of the tubular bag. The hoses for the air, water and suction connections, now contaminated, are placed in the bag or funnel. The bag opening is closed, thus sealing all contaminated parts inside the tubular bag. The contaminated sheath and the bags are discarded as a unit while the sheath is contained within the tubular bag.

BEST MODE FOR CARRYING OUT THE INVENTION

Figures 1, 2:
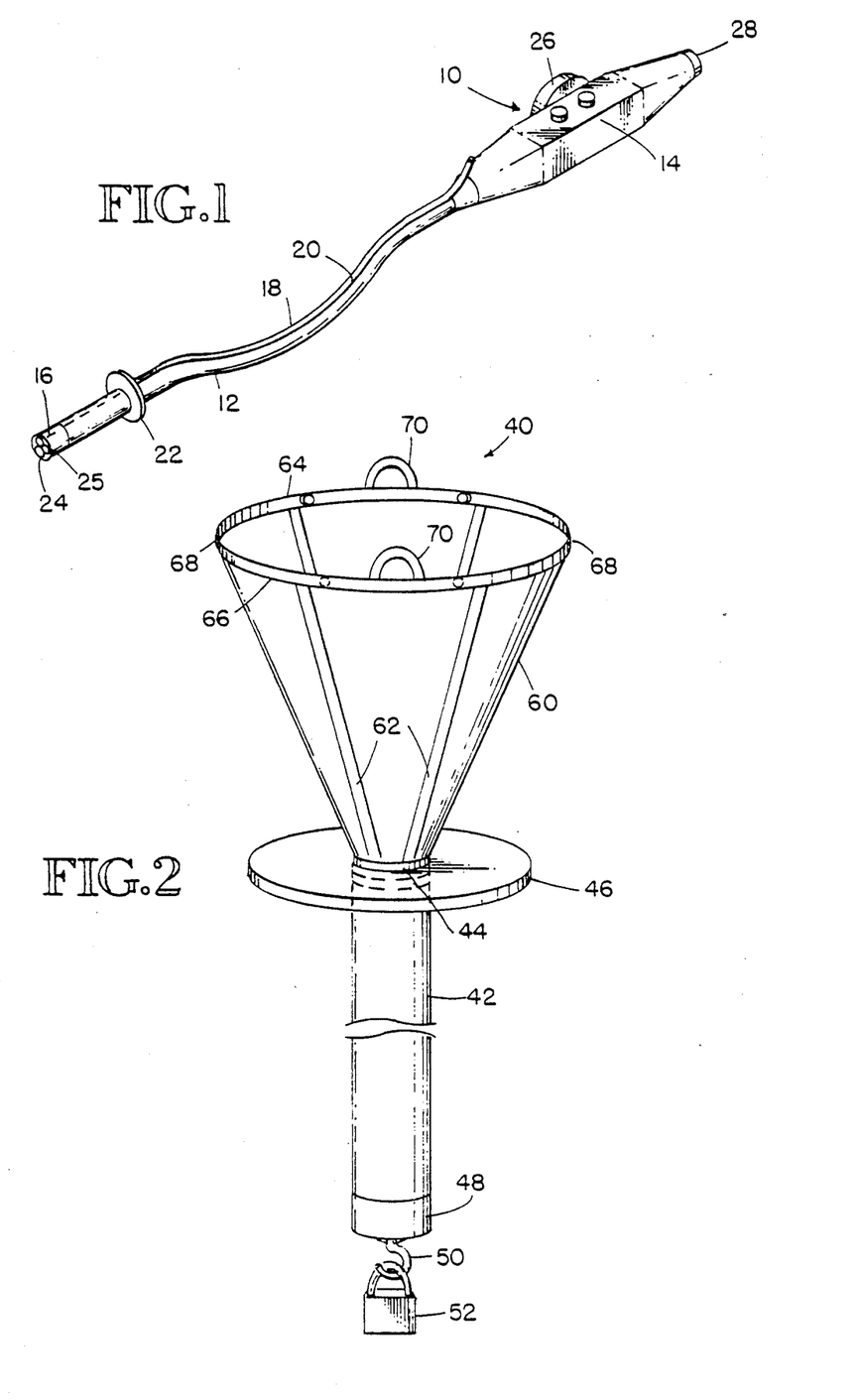
FIG. 1 is an isometric view of an endoscope having a protective endoscope sheath installed on its insertion tube.
FIG. 2 is a side elevational view of the inventive elongated, flexible, nonelastic bag used to package disposable endoscope sheaths before and after use and to facilitate installation on and removal from endoscopes.

An endoscope 10, of the type utilizing a disposable protective endoscope sheath, is illustrated in FIG. 1. The endoscope 19 includes a flexible, elongated insertion tube 12 extending from a control handle 14 to a tip portion 16. An elongated, generally U-shaped groove 18 extends along the length of the insertion tube 12 and the tip portion 16. The groove 18 receives a biopsy channel 20 (and, if desired, water, suction and inflation channels) covered by in a disposable sheath 22 that surrounds the insertion tube 12. The end of the sheath 22 includes an optical window 24 for an imaging system and an illuminating system mounted in the tip portion 16 of the endoscope 10. The optical window 24 is mounted in a rigid cylindrical housing 25 secured to the distal end of the sheath 22. As with conventional endoscopes, the imaging system may be either video or fiber optic. Similarly, the illuminating system may be either electrical or fiber optic. The endoscope 10 also includes a set of control cables (not shown) extending through the insertion tube 12 from the tip portion 16 to the control handle 14 for selectively bending the tip portion 16 as desired. The control cables are operated by conventional control wheels 26 mounted on the control handle 14. The control handle 14 also includes a conventional eyepiece 28, assuming that a fiber optic imaging system is used.

The sheath 22 may be installed on the insertion tube 12 by rolling it onto the tube 12 from the tip portion 16 toward the handle 14. However, this installation technique exhibits several disadvantages. It is therefore preferable to inflate the sheath 22 while it is in its unrolled condition and then insert the insertion tube 12 into the sheath 22 while it is in its inflated condition. A structure for inflating the sheath 22 is described in U.S. Pat. No. 4,646,722 which is incorporated herein by reference.

One embodiment of the packaging system for endoscopes using disposable sheaths is illustrated in FIG. 2. A packaging bag 40 includes an elongated insertion tube bag 42 having a length slightly longer than the length of the insertion tube 12 of the endoscope 10 and a diameter that is substantially larger than the diameter of the insertion tube 12 but within the range of expansion of the sheath material. The insertion tube bag 42 is formed of a flexible but substantially nonelastic material, such as a suitable plastic. The insertion tube bag 42 is suspended from a rigid plastic collar 44 having an outwardly projecting support flange 46. The insertion tube bag 42 terminates in a rigid, cylindrical tip 48 having a hook 50 at its lower end from which a weight 52 is suspended. A funnel-like member 60 projects upwardly from the collar 44. A plurality of relatively rigid stays 62 can be attached to the funnel-like member 60. The stays 62 extend upwardly from the collar 44 to a pair relatively rigid peripheral ribs 64, 66 which intersect each other at a pair of hinge points 68. The hinge points 68 allow the ribs 64, 66 to be folded against each other to collapse the funnel-like member 60 flat to reduce its size for shipping and storage. Also, securing the ribs 64, 66 to each other causes the funnel-like member 60 to assume the configuration of a bag for housing the channels 20 (FIG. 1) forming part of the sheath 22 as well as other supplies and devices that may be used with the endoscope 10 or sheath 22. Alternatively, the funnel-like member 60 may be a collapsible bag for holding various hoses prior to use. The bag 60 may be removed or retracted prior to inserting the endoscope into the sheath.

Figure 7:
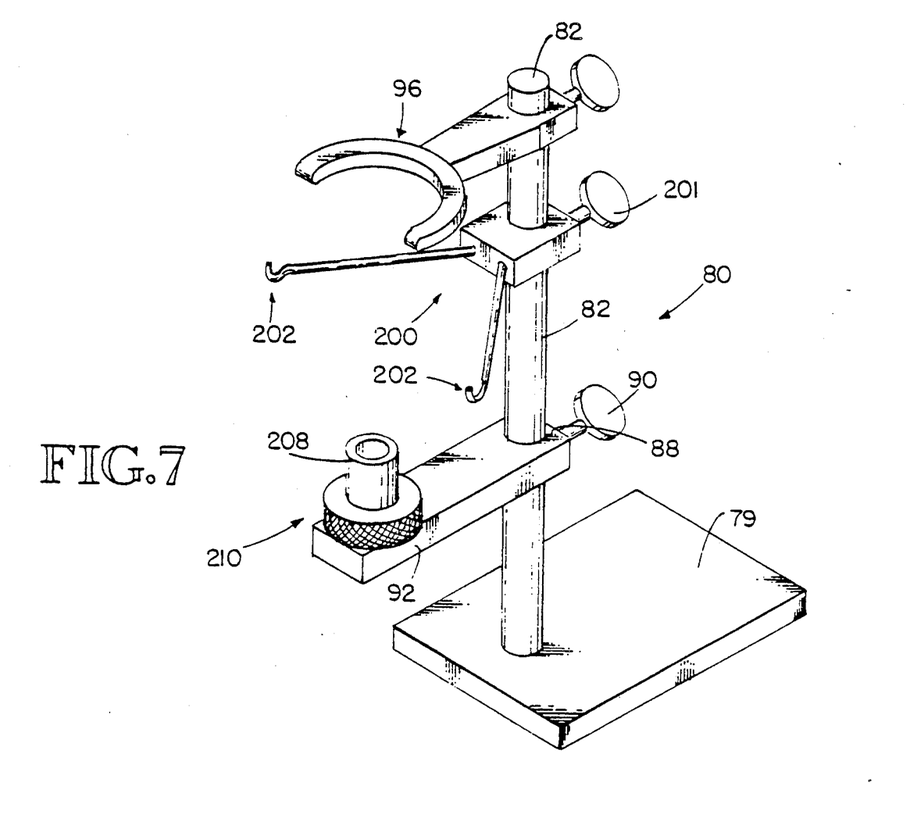
FIG. 7 is an isometric view of an alternative embodiment of the stand for placement on a table.

The funnel-like member 60 is preferably formed from the same type of material as the insertion tube bag 42. However, for the reasons explained below, it may be somewhat thinner. The stays 62 maintain the funnel-like configuration of the funnel-like member 60. The peripheral ribs 64, 66 are used to hold the periphery of the funnel-like member 60 open for insertion and removal of the insertion tube 12 of the endoscope 10. A pair of semicircular tabs 70 project upwardly from the midpoints of the peripheral ribs 64, 66. In the event a collapsible bag is used for member 60, the top edges of the bag may be held up by support rack 200 from tabs 70, by hooking members 202, as shown in FIG. 7. This latter design allows the user to raise and lower the bag 60 as desired. This can be helpful when integrating the sheath to the endoscope by allowing improved access. The user may wish the bag 60 to be held open and extended upward while removing the hoses stored therein. The user may then lower hooking member 202 by loosening clamp 201. This lowers the top of the bag to the support arm 92 to permit the user to directly access the nozzle 80 and tubular bag opening.

As explained in greater detail below, the packaging bag 40 is shipped with a disposable sheath (not shown) extending along the length of the insertion tube bag 42. The sheath is installed onto the insertion tube 12 by inserting the insertion tube 12 into the sheath while the sheath is in the insertion tube bag 42. The insertion tube 12 and sheath 22 are then removed from the bag 42 for use in conducting an endoscopic procedure. After the endoscopic procedure has been completed, the insertion tube 12, surrounded by the sheath 22, is inserted into the insertion tube bag 42, and the insertion tube 12 is removed from the bag 42 while leaving the sheath 22 behind in the insertion tube bag 42.

The manner of using the packaging bag 40 of FIG. 2 is explained in greater detail with reference to FIG. 3. The packaging bag 40 is illustrated in FIG. 3A in the condition in which it is received from the supplier of the sheath. The sheath 22 extends the length of the insertion tube bag 42 from the cylindircal housing 25 to an inflation nozzle 80. The inflation nozzle 80 can be releasably secured to the bag 42 by conventional means (not shown), such as a clip, snap or Velcro fastener, to prevent inadvertent longitudinal movement of the sheath 22 along the length of the bag 42. As illustrated in FIG. 3A, the diameter of the sheath 22 is substantially smaller than the diameter of the insertion tube bag 42. In this condition, the insertion tube bag 42 isolates the sheath 22 from the environment to avoid contamination and to maintain the sterility of the sheath 22.

Figures 3A, 3B, 3C:
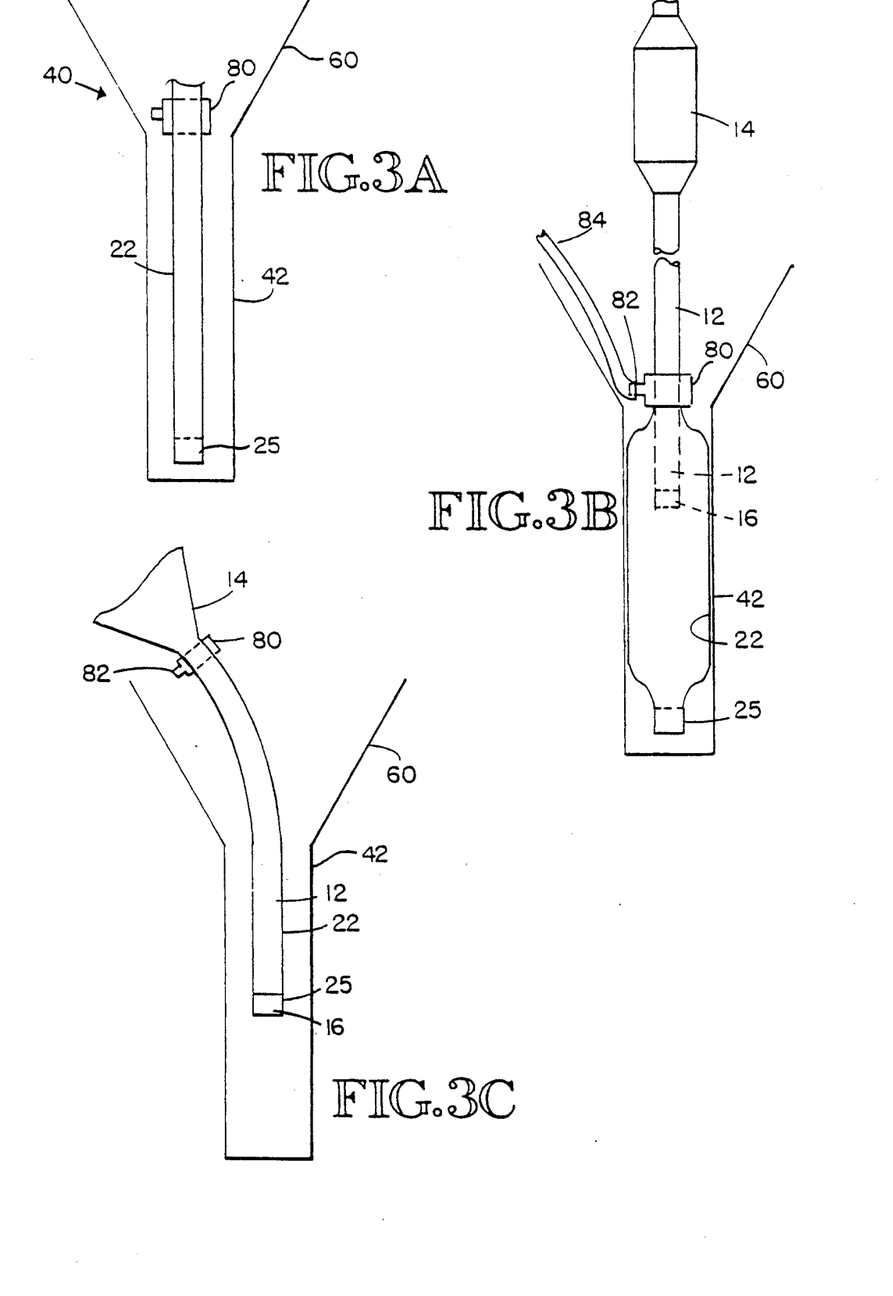
FIGS. 3A-C are schematics showing the technique of using the bag of FIG. 2 to install a disposable sheath on an endoscope prior to use and to remove the sheath from the endoscope after use.

The sheath 22 is installed on the insertion tube 12 of an endoscope, as illustrated in FIG. 3B. A conventional source of pressurized air is connected to an inlet 82 of the nozzle 80 through a tube 84. Air thus flows from inlet 82 into the interior of the sheath 22. The nozzle 80 is made of nonexpandable material. The nozzle 80 may be any suitable nozzle, such as the nozzle shown in Pat. No. 4,646,722. Since the end opening of the nozzle 80 is blocked by the end of the insertion tube 12, the pressure in the sheath 22 builds up. The sheath 22 then expands until its outer surface contacts the inner surface of the insertion tube bag 42. The insertion tube bag 42, by restraining expansion of the sheath 22, reduces the necessity to precisely control both the pressure applied to expand the sheath 22 and the uniformity of the thickness of the sheath 22. If the expansion of the sheath 22 was not prevented by the insertion tube bag 42, excessive pressure applied to the sheath 22 could cause the sheath 22 to burst like a balloon. Also, irregularities in the thickness of the wall of the sheath 22 could cause excessive or insufficient expansion of the sheath 22 in localized areas which could also cause the sheath 22 to rupture or be difficult to use.

Once the sheath 22 has expanded to the diameter of the insertion tube bag 42, the insertion tube 12 can be easily further inserted into the sheath 22 through the opening in the nozzle 80, as illustrated in FIG. 3B.

After the insertion tube 12 has been inserted all the way into the sheath 22, the air pressure is removed from the nozzle 80 thereby allowing the sheath 22 to deflate. The tube 84 is then removed from the inlet 82 of the nozzle 80. The endoscope may then be used by removing the insertion tube 12 and sheath 22 from the insertion tube bag 42, as illustrated in FIG. 3C. Aternatively, the insertion tube 12 and sheath 22 may remain in the insertion tube bag 42 until it is ready for use. In this condition, the insertion tube bag 42 can maintain the sterility or cleanliness of the sheath 22. Also, of course, the insertion tube 12, surrounded by the sheath 22, may be inserted into the bag 42 during an endoscopic procedure or examination thereby storing the endoscope in a manner that prevents the spread of contamination in the examining room environment. This may be desirable in the situation where the endoscope is temporarily removed from the patient.

After the insertion tube 12 and sheath 22 have been used to conduct an endoscopic procedure, the outer surface of the sheath 22 as well as the channels 20 are contaminated. It is important to prevent this contamination from being spread around the examining room environment as the sheath 22 is removed from the insertion tube 12. The sheath 22 may be removed from the insertion tube 12 without spreading contamination by reinserting the insertion tube 12 and sheath 22 into the insertion tube bag 42, as illustrated in FIG. 3C. Air pressure is then applied to the inlet 82 of the nozzle 80 through the tube 84 to inflate the sheath 22. The sheath 22 then expands away from the outer surface of the insertion tube 12 against the inner surface of the insertion tube bag 42, as illustrated in FIG. 3B. Once the sheath 22 has expanded to the diameter of the insertion tube bag 42, the insertion tube 12 may be removed from the sheath 22 with the same ease in which it was installed, as illustrated in FIG. 3B. The air pressure is then removed from the sheath 22 to allow the sheath 22 to deflate, as illustrated in FIG. 3A. The top of the bag assembly 40 is closed. The contaminated sheath 22 can then be discarded with the insertion tube bag 42 preventing the contamination from spreading to the environment.

As mentioned above, the nonresilient characteristic of the insertion tube bag 42 restricts further expansion of the sheath 22 once the sheath expands to the diameter of the bag 42. The bag 42 restricts expansion of the sheath 22 during both the insertion of the insertion tube 12 into the sheath 22 and the removal of the insertion tube 12 from the sheath 22. However, it is even more important to prevent an explosive rupture of the sheath 22 during the removal of the insertion tube 12 from the sheath 22 because an explosive rupture of the sheath 22 during the removal phase could spread contamination over a wide area. In order to adequately restrict expansion of the sheath 22, the bag 42 should be relatively sturdy. For typical, commercially available plastic films, the bag 42 should have a wall thickness of at least 0.004 inch of polyethylene or other suitable material. In contrast, since the funnel-like member 60 is not forced outwardly by inflation of the sheath 22, it may have a wall thickness of about 0.001 inch to 0.002 inch.

The length of a typical insertion tube 12 is on the order of 1 meter, and insertion tubes for colonoscopes can have lengths of as long as 2 meters.

Figure 6:
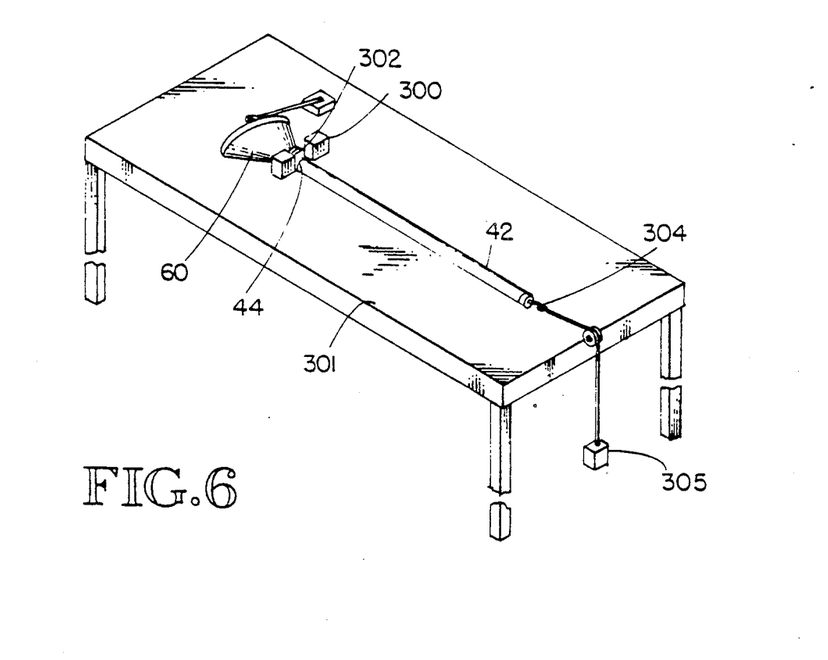
FIG. 6 is an isometric view of an alternative embodiment holding the tubular bag in the horizontal position.

It can be difficult to support an insertion tube bag 42 having a length of between 1 and 2 meters in a vertical manner. Consequently, it may be desirable to support the insertion tube bag 42 in a horizontal fashion on table 301, as shown in FIG. 6. In this embodiment, the insertion tube bag 42 extends along table 301 between a forked support rack 300 on a tab 302, and a hook 304., The hook may be loaded with a suitable tensioning device 305 (spring or weight) if desired, or may be a rigid coupling.

Figure 4:
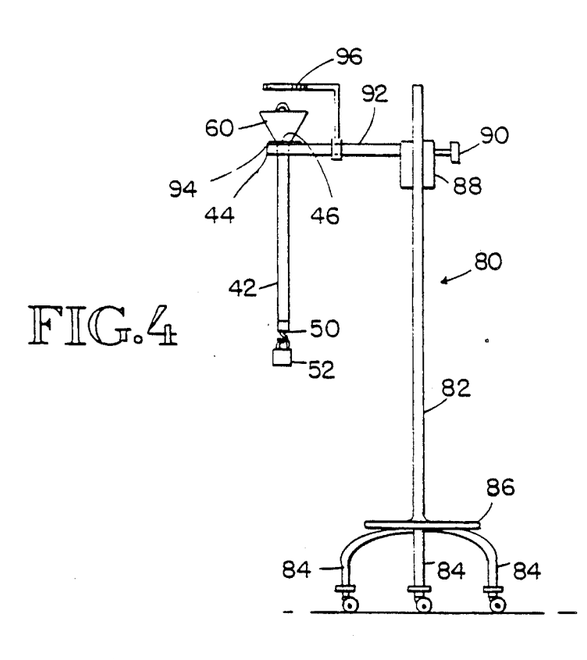
FIG. 4 is a side elevational view showing the packaging bag of FIG. 2 mounted on a stand that is used to support the bag as an endoscope is inserted into and removed from the bag.

For an endoscope with a length of 1 meter or less, it may be desirable to use a stand 80 as illustrated in FIGS. 4 and 7. This stand could extend to the floor, as shown in FIG. 4, or sit on a bench, as shown in FIG. 7. The elements and features of each are interchangeable. The stand 80 includes a vertical support bar 82 projecting vertically from the base 79 or from three legs 84 interconnected by a reinforcing ring 86. A clamp 88 includes a hand screw 90 for frictionally engaging the support member 82 in a releasable manner, A support arm 92 has a forked end 94 that supports the tube 40 at support flange 46, as shown in FIGS. 2 and 4. Thus, the support arm 92 holds the collar 44 up through the support flange 46. Alternatively, as shown in FIG. 7, a collet closure 208 may be used to support collar 44 rather than using a forked member 94. When a large bag is used without support ribs, it is sometimes advantageous to retract the bag or funnel member below the sheath manifold which extends just above support collar 44 (not shown). Having the collet 208 extend above support member 92 holds the collar 44 a dsired distance above member 92. This permits the bag member 60 to be retracted below the top of the support collar 44 such as by folding bag 60 or by lowering clamp 200. This improves access to the sheath manifold (not shown) for scope insertion and removal.

A forked holder 96 projects horizontally from support bar 82 above the support arm 92. Member 60 allows the handle 14 (FIG. 1) of the endoscope to clip into the forked holder 96 while the insertion tube 12 is left in the insertion tube bag 42 for subsequent use or disposal.

The weight 52, illustrated in FIGS. 2 and 4, tensions the insertion tube bag 42 to prevent the sheath 22 from clinging to the bag 42 when the sheath 22 and insertion tube 12 are being removed from or reinserted into the bag 42. While the bag 42 is of an expandable material, it may be made of collapsible material. A weight of about 200 grams should be sufficiently heavy to adequately anchor the end of the bag 42. Alternatively, bag 42 may be a stiffer member and not require a weight.

The stand 80 illustrated in FIGS. 4 and 7 may be advantageously used for endoscopes 10 having insertion tubes 12 of up to about 1 meter. Endoscopes 10 having longer insertion tubes 12 may require that the bag 42 by positioned in an inclined or horizontal position on a table, as shown in FIG. 6. In this embodiment a tension spring (not shown) extending between the distal end of the insertion tube bag 42 and a fixed support may be used instead of the weight 52 to ensure that bag 42 is completely extended.

Figure 5:
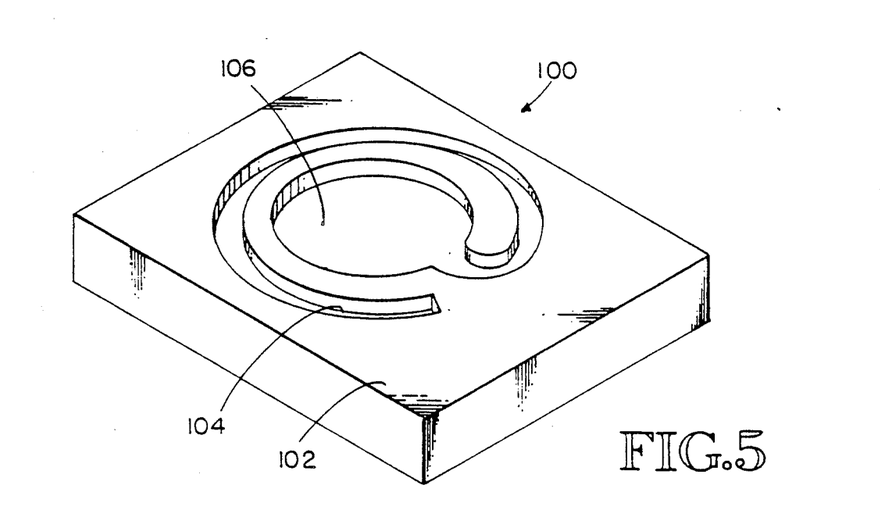
FIG. 5 is an isometric view of a sterile tray used to package the bag of FIG. 2 containing a disposable endoscope sheath prior to installation on an endoscope. This can also be used to dispose of the contaminated sheath inside the packaging bag after use.

In order to prevent contamination and/or maintain the sterility of the sheath 22 prior to use and to prevent damage while shipping, it is important to package the packaging bag 40 for shipment and storage in a suitable container. The substantial length of the insertion tube bag 42 makes it undesirable to utilize a linear package for the packaging bag 40 since it is difficult to transport and store relatively long objects. Instead, the insertion tube bag 42 having sheath 22 therein may be placed in a tray 100 of the type illustrated in FIG. 5. The tray 100 includes a container 102 having a spiral recess 104 of a length and width adapted to receive the insertion tube bag 42 in a coiled configuration. A circular recess 106 formed at the center of the container 102 receives the funnel-like or bag member 60. The bag member 60 includes additional hoses to be coupled to and disposed with sheath 22. The container 102 may be covered by a paper or plastic membrane sealed to the container 102 with a pressure-sensitive adhesive. The packaging bag 40 can be sterilized in the container 102 by suitable means, such as by flooding the container 102 with ethylene oxide gas.

When the sheath 22 is to be installed on the insertion tube 12 of an endoscope, the paper or plastic membrane can be peeled from the upper surface of the container 102, thereby allowing the insertion tube bag 42 and funnel-like member 60 to be removed from the respective recesses 104, 106. The packaging bag 40 is then mounted at collar 44 on the stand 80 (FIG. 4 or 7, or table 301) and the weight 52 is attached to its lower end. The insertion tube 12 is then inserted into the sheath 22 as explained above with reference to FIG. 3B. After the sheath 22 has been installed on the insertion tube 12, the insertion tube 12 and sheath 22 are removed from the bag 42, and an endoscopic procedure or exam is conducted. After the endoscopic procedure or exam has been completed, the insertion tube 12 and sheath 22 are reinserted into the insertion tube bag 42, the sheath 22 is inflated and the insertion tube 12 is then removed from the sheath 22. The contaminated sheath 22 inside the insertion tube bag 42 can then be disposed of either directly or after once again placing the insertion tube bag 42 and funnel-like member 60 in the respective recesses 104, 106 of the tray 100.

Is is thus seen that the inventive packaging system prevents the sheath from becoming contaminated prior to use, and it prevents the spread of contamination as the sheath is being removed from the endoscope after use and during disposal of the contaminated sheath. The bag further facilitates the installation of the sheath on the endoscope and the removal of the sheath from the endoscope after use. Further, the packaging system can be easily adapted for use with endoscope sheaths having a wide variety of shapes and sizes and special functioning designs.

We claim:

1. A packaging system for a disposable endoscope sheath adapted for use with an endoscope having a handle and an insertion tube, comprising:
   an elongated bag having a distal end and a proximal end, said bag being closed at its distal end and open at its proximal end, said bag further including a funnellike member extending from the perimeter of said bag adjacent its proximal end, said funnel-like member flaring outwardly away from the opening in the proximal end of said bag, said funnel-like member further including a plurality of relatively rigid stays extending from the proximal end of said bag toward the edge of said funnellike member to maintain said funnel-like configuration of said member; and
   a disposable, resilient endoscope sheath positioned within said bag and extending substantially along the length thereof, said sheath having an open end positioned near the proximal end of said bag so that said sheath can be installed on said insertion tube by inserting said insertion tube through the proximal opening in said bag. and the opening in said sheath.

2. The packaging system of claim 1 wherein said funnel-like member further includes a pair of pivotally interconnected, relatively rigid ribs extending along the edges of said funnel-like member.

3. A packaging system for a disposable endoscope sheath adapted for use with an endoscope having a handle and an insertion tube, comprising:
   an elongated bag having a distal end and a proximal end, said bag being closed at its distal end and open at its proximal end, said bag further including a funnellike member extending from the perimeter of said bag adjacent its proximal end, said funnel-like member flaring outwardly away from the opening in the proximal end of said bag, said funnel-like member including a stiffening rib around the opening of said funnel-like member to assist in maintaining the open position; and
   a disposable, resilient endoscope sheath positioned within said bag and extending substantially along the length thereof, said sheath having an open end positioned near the proximal end of said bag so that said sheath can be installed on said insertion tube by inserting said insertion tube through the proximal opening in said bag and the opening in said sheath.

4. A packaging system for a disposable endoscope sheath adapted for use with an endoscope having a handle and an insertion tube, comprising:
   an elongated bag having a distal end and a proximal end, said bag being closed at its distal end and open at its proximal end, said bag further including a funnellike member extending from the perimeter of said bag adjacent its proximal end, said funnel-like member flaring outwardly away from the opening in the proximal end of said bag, said bag further including a rigid cylindrical collar extending around the periphery of said bag adjacent the proximal end of said bag between said bag and said funnel-like member; and
   a disposable, resilient endoscope sheath positioned with said bag and extending substantially along the length thereof, said sheath having an open end positioned near the proximal end of said bag so that said sheath can be installed on said insertion tube by inserting said insertion tube through the proximal opening in said bag and the opening in said sheath.

5. The packaging system of claim 4 further including an annular support flange extending around said collar and projecting outwardly therefrom so that said bag can be supported through said collar and support flange.

6. A packaging system for a disposable endoscope sheath adapted for use with an endoscope having a handle and an insertion tube, comprising:
   an elongated bag having a distal end and a proximal end, said bag being closed at its distal end and open at its proximal end, the distal end of said bag terminating in a relatively rigid, cylindrical end cap; and
   a disposable, resilient endoscope sheath positioned within said bag and extending substantially along the length thereof, said sheath having an open end positioned near the proximal end of said bag so that said sheath can be installed on said insertion tube by inserting said insertion tube through the proximal opening in said bag and the opening in said sheath.

7. The packaging system of claim 6 further including an anchor weight suspended from said end cap to maintain said insertion tube bag in an extended configuration.

8. A packaging system for a disposable endoscope sheath adapted for use with an endoscope having a handle and an insertion tube, comprising:
   an elongated bag having a distal end and a proximal end, said bag being closed at its distal end and open at its proximal end;
   a disposable, resilient endoscope sheath positioned within said bag and extending substantially along the length thereof, said sheath having an open end positioned near the proximal end of said bag so that said sheath can be installed on said insertion tube by inserting said insertion tube through the proximal opening in said bag and the opening in said sheath;
   a circular, flexible member coupled at the proximal end of said bag for holding accessory tubes for said sheath;
   a first support member for supporting said bag at said distal end; and
   a second support member for supporting said circular, flexible member above said bag.

9. The packaging system of claim 8 wherein said second support member is movable relative to said first support member.

10. A packaging system for a disposable endoscope sheath adapted for use with an endoscope having a handle and an insertion tube, comprising:
    an elongated bag having a distal end and a proximal end, said bag being closed at its distal end and open at its proximal end, said bag further including a funnellike member extending from the perimeter of said bag adjacent its proximal end, said funnel-like member flaring outwardly away from the opening in the proximal end of said bag; and
    a disposable, resilient endoscope sheath positioned within said bag and extending substantially along the length thereof, said sheath having an open end positioned near the proximal end of said bag so that said sheath can be installed on said insertion tube by inserting said insertion tube through the proximal opening in said bag and the opening in said sheath, said sheath further including a plurality of accessory tubes positioned within said funnel-like member.

* * * * *